United States Patent [19]

Forbus

[11] Patent Number: 4,547,618
[45] Date of Patent: Oct. 15, 1985

[54] MODIFIED ZSM-12 CATALYSTS AND PROCESSES FOR CONVERSION OF PROPANE TO PROPYLENE

[75] Inventor: Nancy P. Forbus, Newtown, Pa.

[73] Assignee: Mobil Oil Corporation, New York, N.Y.

[21] Appl. No.: 686,961

[22] Filed: Dec. 28, 1984

[51] Int. Cl.[4] .......................... C07C 5/26; C07C 5/40
[52] U.S. Cl. ..................................... 585/660; 502/71; 502/74; 585/661
[58] Field of Search ............................ 502/71, 74, 77; 585/660, 661

[56] References Cited

U.S. PATENT DOCUMENTS

| 3,665,049 | 5/1972 | Cornelius et al. | 585/662 |
|---|---|---|---|
| 3,686,340 | 8/1972 | Patrick et al. | 585/485 |
| 3,718,607 | 2/1973 | Martin | 502/222 |
| 3,759,821 | 9/1973 | Brennan et al. | 208/93 |
| 3,778,388 | 12/1973 | Cornelius et al. | 502/320 |
| 3,832,449 | 8/1974 | Rosinski et al. | 423/328 |
| 3,957,686 | 5/1976 | Duhaut et al. | 208/138 |
| 4,148,835 | 4/1979 | Chen et al. | 585/640 |
| 4,278,565 | 7/1981 | Chen et al. | 502/74 |
| 4,349,461 | 9/1982 | Chu et al. | 502/74 |
| 4,450,313 | 5/1984 | Eastman et al. | 585/624 |

Primary Examiner—D. E. Gantz
Assistant Examiner—A. Pal
Attorney, Agent, or Firm—Alexander J. McKillop; Michael G. Gilman; Edward F. Kenehan, Jr.

[57] ABSTRACT

There is provided a catalyst comprising ZSM-12 and two modifiers. The modifiers are (i) magnesium and/or manganese and (ii) platinum. There is also provided a process for converting propane to propylene by a dehydrogenation reaction with this catalyst.

9 Claims, No Drawings

MODIFIED ZSM-12 CATALYSTS AND PROCESSES FOR CONVERSION OF PROPANE TO PROPYLENE

BACKGROUND

This invention relates to ZSM-12 catalysts modified with (i) magnesium and/or manganese and (ii) platinum. These catalysts are especially selective when used in the conversion of propane to propylene.

The Cornelius et al U.S. Pat. No. 3,665,049, the Patrick et al U.S. Pat. No. 3,686,340, the Martin U.S. Pat. No. 3,718,607 and the Cornelius et al U.S. Pat. No. 3,778,388, the entire disclosures of which are expressly incorporated herein by reference, each describe processes for converting propane to propylene using catalysts different from those of the present invention.

The Rosinski et al U.S. Pat. No. 3,832,449, the entire disclosure of which is expressly incorporated herein by reference, describes the zeolite, ZSM-12. This Rosinski et al patent indicates that ZSM-12 has ion exchange capacity with a wide variety of metal cations including manganese, calcium and other metals of Group II of the Periodic Table. Note column 5, lines 38–47, of this Rosinski et al patent. This Rosinski et al patent also indicates that ZSM-12 can be combined with certain metals such as platinum for hydrogenation-dehydrogenation reactions. Note column 7, lines 44–47, of this Rosinski et al patent.

The Brennan et al U.S. Pat. No. 3,759,821 indicates that optional hydrogenation/dehydrogenation components for incorporation with the zeolites described therein, e.g., ZSM-5, include metals, oxides and sulfides of a wide variety of metals including manganese. Note column 7, line 57 to column 8, line 14, especially column 8, line 9, of this Brennan et al patent.

Published European patent application No. 0 105 591, which claims priority to U.S. application Ser. No. 429,933, filed Sep. 30, 1982, the entire disclosures of said applications also being expressly incorporated herein by reference, describes the conversion of methanol to light olefins especially enriched in propylene using a ZSM-12 catalyst modified with magnesium and/or manganese.

SUMMARY

According to one aspect of the invention, there is provided a catalyst comprising ZSM-12, said catalyst further comprising:
(i) a magnesium and/or manganese modifier; and
(ii) a platinum modifier.

According to another aspect of the invention, there is provided a process for converting propane to propylene with this catalyst. This process comprises contacting propane under sufficient dehydrogenation conditions with this catalyst.

EMBODIMENTS

It is to be understood that by incorporating by reference the foregoing Rosinski et al U.S. Pat. No. 3,832,449 to describe, e.g., examples of specific members of the specified zeolite ZSM-12 class with greater particularity, it is intended that identification of the therein disclosed crystalline zeolite ZSM-12 be resolved on the basis of its respective X-ray diffraction patterns. The present invention contemplates utilization of such catalysts wherein the mole ratio of silica to alumina is essentially unbounded. The incorporation of the identified patent should therefore not be construed as limiting the disclosed crystalline zeolites to those having the specific silica-alumina mole ratios discussed therein, it now being known that such zeolites may be substantially aluminum-free and yet, having the same crystal structure as the disclosed materials, may be useful or even preferred in some applications. It is the crystal structure, as identified by the X-ray diffraction "fingerprint", which establishes the identity of the specific crystalline ZSM-12 zeolite material. Furthermore, the ZSM-12 zeolites of the present invention preferably have a crystal size of from e.g., about 0.02 to 0.5 micron.

The specific zeolite ZSM-12, when prepared in the presence of organic cations, is substantially catalytically inactive, possibly because the intra-crystalline free space is occupied by organic cations from the forming solution. The zeolite may be activated by heating in an inert atmosphere at 540° C. for one hour, for example, followed by base exchange with ammonium salts followed by calcination at 540° C. in air. The presence of organic cations in the forming solution may not be absolutely essential to the formation of this type zeolite; however, the presence of these cations does appear to favor the formation of this special class of zeolite. More generally, it is desirable to activate this type catalyst by base exchange with ammonium salts and subsequently by treatment with platinum, magnesium and manganese salts as hereinafter described, followed by calcination in air at about 540° C. for from about 15 minutes to about 24 hours.

In a preferred aspect of this invention, the ZSM-12 zeolites herein are selected as those providing among other things a crystal framework density, in the dry hydrogen form, of not less than about 1.6 grams per cubic centimeter. The dry density for known structures may be calculated from the number of silicon plus aluminum atoms per 1000 cubic Angstroms, as given, e.g., on Page 19 of the article ZEOLITE STRUCTURE by W. M. Meier. This paper, the entire contents of which are incorporated herein by reference, is included in PROCEEDINGS OF THE CONFERENCE ON MOLECULAR SIEVES, (London, April 1967) published by the Society of Chemical Industry, London, 1968.

When the crystal structure is unknown, the crystal framework density may be determined by classical pyknometer techniques. For example, it may be determined by immersing the dry hydrogen form of the zeolite in an organic solvent which is not sorbed by the crystal. Or, the crystal density may be determined by mercury porosimetry, since mercury will fill the interstices between crystals but will not penetrate the intracrystalline free space.

Crystal framework densities of some typical zeolites, including others besides the ZSM-12 utilized in this invention, are:

|  | Void Volume | Framework Density |
| --- | --- | --- |
| Ferrierite | 0.28 cc/cc | 1.76 g/cc |
| Mordenite | .28 | 1.7 |
| ZSM-5, -11 | .29 | 1.79 |
| ZSM-12 | — | 1.8 |
| ZSM-23 | — | 2.0 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |

-continued

| | Void Volume | Framework Density |
| --- | --- | --- |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the ZSM-12 zeolite is conveniently converted to the ammonium form as a result of ammonium ion exchange. This ammonium form of ZSM-12 may be employed as a precursor to the modified zeolites used in the process of the present invention.

The ZSM-12 zeolite used in the present invention may have an activity in terms of an alpha value of between about 25 and 250, e.g., between about 50 and 150. The alpha value reflects the relative activity of the catalyst with respect to a high activity silica-alumina cracking catalyst. To determine the alpha value, as such term is used herein, n-hexane conversion is determined at about 1000° F. Conversion is varied by variation in space velocity such that a conversion level of 10 to 60 percent of n-hexane is obtained and converted to a rate constant per unit volume of zeolite and compared with that of silica-alumina catalyst which is normalized to a reference activity of 1000° F. Catalytic activity of the catalysts are expressed as multiple of this standard, i.e. the silica-alumina standard. The silica-alumina reference catalyst contains about 10 weight percent $Al_2O_3$ and remainder $SiO_2$. This method of determining alpha is more fully described in the Journal of Catalysis, Vol. VI, Pages 278–287, 1966, incorporated herein by reference.

In practicing the propane conversion process of the present invention, it may be useful to incorporate the above-described crystalline ZSM-12 zeolites with a matrix comprising another material resistant to the temperature and other conditions employed in the process. Such matrix material is useful as a binder and imparts greater resistance to the catalyst for the temperature, pressure and reactant feed stream velocity conditions which may be encountered in the propane conversion process.

Useful matrix materials include both synthetic and naturally occurring substances, as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the ZSM-12 zeolites employed herein may be composited with a porous matrix material, such as alumina, silica-alumina, silica-magnesia, silica-zirconia, silica-thoria, silica-beryllia, and silica-titania, as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix, on an anhydrous basis, may vary widely with the zeolite content ranging from between about 1 to about 99 percent by weight and more usually in the range of about 5 to about 80 percent by weight of the dry composite.

The ZSM-12 zeolite catalysts herein are modified by incorporating thereon a minor proportion of magnesium and/or a minor proportion of manganese. Such modified zeolite composites can be prepared by contacting the ZSM-12 zeolite composition with one or more compounds or complexes of the elements magnesium and manganese and by preferably thereafter heating the catalyst composite to convert the modifying elements to their oxide form. Incorporation can occur by the mechanisms of ion exchange, adsorption and/or impregnation, the latter two phenomena commonly being referred to as "stuffing." It should be emphasized that, while ion exchange can be used to incorporate the modifying metals onto the zeolite compositions described herein, ion exchange alone will generally not provide the requisite amount or form preferred (i.e. the oxide form) of incorporated magnesium and manganese onto the zeolite catalyst composites used in the present invention. More particularly, the amount of magnesium and/or manganese plus platinum may exceed the amount capable of occupying all of the cation exchange sites of the ZSM-12 by a factor of, e.g., 2 or more or even 5 or more.

Generally, the zeolite composites of the present invention can be modified by contacting such composites with solutions of compounds of the magnesium and manganese metals to be incorporated. Such solutions may be formulated from any suitable solvent which is inert with respect to the metal-containing compound and the zeolite composition. Nonlimiting examples of some suitable solvents include water, aromatic and aliphatic hydrocarbons, alcohols, and organic acids (such as acetic acid, formic acid, propionic acid and so forth). Other commonly available solvents such as halogenated hydrocarbons, ketones, ethers, etc., may also be useful to dissolve some magnesium or manganese compounds or complexes. Generally, the most useful solvent will be found to be water. However, the solvent of choice for any particular Mg or Mn compound will, of course, be determined by the nature of that compound, and for that reason the foregoing list should not be considered exhaustive of all of the suitable possibilities.

Treating compounds are those which contain the elements magnesium or manganese, the two catalyst modifiers used in the present invention. Representative magnesium-containing compounds include magnesium acetate, magnesium nitrate, magnesium benzoate, magnesium propionate, magnesium 2-ethylhexanoate, magnesium carbonate, magnesium formate, magnesium oxylate, magnesium amide, magnesium bromide, magnesium hydride, magnesium lactate, magnesium laurate, magnesium oleate, magnesium palmitate, magnesium salicylate, magnesium stearate and magnesium sulfide.

Representative manganese-containing compounds include manganese acetate, manganese nitrate, manganese lactate, manganese oxalate, manganese carbonate, manganese citrate, manganese tartarate, manganese bromide, manganese chloride, manganese sulfate, and manganese sulfide. The platinum component may be added to the ZSM-12 separately or along with the addition of the magnesium and/or manganese component. This platinum component may be incorporated into the ZSM-12 by treating the zeolite with a solution containing a platinum metal-containing ion. Thus, suitable platinum compounds include chloroplatinic acid, platinous chloride and various compounds containing the platinum ammine complex.

The amount of modifying metal incorporated onto the zeolite composition by reaction with these metal-containing compounds will depend upon several factors. One of these is the reaction time, i.e., the time that the ZSM-12 zeolite composition and the metal-containing source are maintained in contact with each other. With greater reaction times, all other factors being equal, a greater amount of metal is incorporated with the zeolite. Other factors upon which the amount of modifiers incorporated with the zeolite is dependent include reaction temperature, concentration of the treating compound in the reaction mixture, the degree to which the zeolite composition has been dried prior to reaction with the metal-containing compounds, the conditions of drying of the zeolite composition after reaction with the treating compounds, and the amount and type of binder incorporated with the zeolite composition.

After modifying metals have been incorporated into the zeolite composite to the extent desired, the metal containing composite can be heated subsequent to metal modification and prior to use. Such heating can be carried out in the presence of oxygen, for example, in air. Although heating may be carried out at a temperature of about 150° C., higher temperatures, e.g., up to about 500° C., are preferred. Heating is generally carried out for 1–5 hours but may be extended to 24 hours or longer. While heating temperatures above about 500° C. may be employed, they are generally not necessary. After the metal-containing composite is heated in air at elevated temperatures, it is contemplated that the modifying metals are actually present at least in part in the zeolite composite in an oxidized state, such as MgO and MnO.

The zeolite composites herein are treated with the foregoing compounds and subsequently heated, under conditions and for a time sufficient to incorporate a minor proportion of each of the modifying elements onto the zeolite composite. Generally, modifying metals are incorporated to the total extent of from about 0.1% to 10% by weight of the zeolite composite, calculated on the basis of the elemental metals. For magnesium as modifying agent, the composite can advantageously comprise from about 0.1% to about 10%, more preferably from about 0.1% to 5%, by weight of magnesium. For manganese as modifying agent, the zeolite composite can advantageously comprise from about 0.1% to 10%, more preferably from about 1% to 10%, by weight manganese. The platinum modifying agent may comprise, e.g., at least 0.1 percent by weight, more particularly, from about 0.1 to about 2 percent by weight of the zeolite composite.

The modified ZSM-12 catalysts of the present invention are capable of exhibiting a high degree of selectivity when used to convert propane to propylene. For example, products of such a propane conversion may contain 75 percent by weight of propylene. This high degree of propylene selectivity may be maintained even at propane conversion rates as high as, e.g., 20 percent or more. In other terms, all things otherwise being equal, the modified ZSM-12 catalyst of the present invention may increase the weight percent of propylene in the conversion products by a factor of, e.g., at least 2.5 times in comparison with an unmodified ZSM-12 catalyst at the same or even higher conversion rates for the modified ZSM-12 catalyst, wherein the unmodified ZSM-12 catalyst has essentially all of the ZSM-12 in the hydrogen form (i.e., HZSM-12).

Propane may be converted to propylene with the modified ZSM-12 catalyst of this invention under sufficient dehydrogenation conditions. These conditions may include, for example, a temperature of from about 300° C. to about 700° C., a pressure of from about 0.1 atmosphere to about 10 atmospheres and a weight hourly space velocity of propane of from about 0.1 to about 20.

COMPARATIVE EXAMPLE A 5.0 gm of an HZSM-12 extrudate (65% zeolite/35% aluminum binder) was centered in a quartz microreactor. Propane was passed over the catalyst at the rate of 40 cc/min. Reactor temperature was maintained at 550° C. The catalyst was then calcined at 538° C. for at least an hour. Screening for propane conversion was then repeated at 600° C. Reactor effluent composition was determined by gas chromatography using a silica gel column for light gas separation and an OV-101 column for a total reactor effluent analysis. Product selectivities and propane conversions were as follows:

| Temperature, °C. | 550° | 600° |
| --- | --- | --- |
| Products, wt. % | | |
| $H_2$ | 1.6 | 3.1 |
| $CH_4$ | 29.3 | 27.1 |
| $C_2H_6$ | 10.1 | 7.0 |
| $C_2H_4$ | 32.4 | 31.5 |
| $C_3H_6$ | 16.5 | 28.6 |
| $C_4H_{10}$ | 4.9 | 1.8 |
| $C_4H_8$ | 5.3 | 0 |
| Bz | 0 | 0.7 |
| Tol | 0 | 0 |
| $C_8A$ | 0 | 0 |
| $C_9A$ | 0 | 0 |
| $C_{10}+$ | 0 | 0 |
| Propane Conversion | 14.2 | 18.4 |

EXAMPLE 1

A catalyst was prepared by adding 10 ml of a solution containing deionized water, 0.7 gm of a 10% solution of $H_2PtCl_6 \cdot 6H_2O$, and 1.6 gm of a 50% solution of $Mn(NO_3)_2$ to 5 gm of the ZSM-12 extrudate used in Comparative Example A. Water was permitted to evaporate slowly (e.g., overnight). The resulting catalyst was calculated to contain 5% Mn and 0.5% Pt by weight. After drying at 75° C., the catalyst was calcined at 500° C. in a muffle furnace 5.0 gm of the resulting catalyst was loaded into a quartz microreactor, reduced under $H_2$ at 500° C., then screened for activity for propane conversion at 550° and 600° C. at a propane WHSV=0.9 hr.$^{-1}$. Product selectivities and propane conversions were as follows:

| Temperature, °C. | 550° | 600° |
| --- | --- | --- |
| Products, wt. % | | |
| $H_2$ | 5.3 | 5.0 |
| $CH_4$ | 1.6 | 5.5 |
| $C_2H_6$ | 3.1 | 4.4 |
| $C_2H_4$ | 0.2 | 2.7 |
| $C_3H_6$ | 84.0 | 78.9 |

-continued

| Temperature, °C. | 550° | 600° |
|---|---|---|
| $C_4H_{10}$ | 0.7 | 0 |
| $C_4H_8$ | 3.1 | 2.2 |
| Bz | 1.8 | 1.0 |
| Tol | 0 | 0 |
| $C_8A$ | 0 | 0 |
| $C_9A$ | 0 | 0 |
| $C_{10}+$ | 0 | 0 |
| Propane Conversion | 23.8 | 26.8 |

EXAMPLE 2

Another catalyst was prepared by adding 10 ml of a solution containing deionized water, 0.7 gm of a 10% solution of $H_2PtCl_6 \cdot 6H_2O$, and 2.6 gm $Mg(NO_3)_2 \cdot 6H_2O$ to 5 gm of the ZSM-12 extrudate used in Comparative Example A. Water was permitted to evaporate slowly (e.g., overnight). The resulting catalyst was dried at 75° C. then calcined at 500° C. in a muffle furnace. This catalyst was calculated to contain 5% Mg and 0.5% Pt. by weight. 5.0 gm of this catalyst was loaded into a quartz microreactor, reduced under $H_2$ at 500° C., then screened for activity in propane conversion at 550° and 600° C. at a propane WHSV=0.9 hr.$^{-1}$. Product selectivities and propane conversions were as follows:

| Temperature, °C. | 550° | 600° |
|---|---|---|
| Products, wt. % | | |
| $H_2$ | 4.6 | 3.9 |
| $CH_4$ | 2.4 | 6.9 |
| $C_2H_6$ | 2.7 | 5.8 |
| $C_2H_4$ | 0.1 | 1.5 |
| $C_3H_6$ | 87.1 | 79.3 |
| $C_4H_{10}$ | 0.5 | 0 |
| $C_4H_8$ | 1.5 | 1.6 |
| Bz | 0 | 0 |
| Tol | 1.1 | 0.8 |
| $C_8A$ | 0 | 0 |
| $C_9A$ | 0 | 0 |
| $C_{10}+$ | 0 | 0 |
| Propane Conversion | 22.7 | 32.0 |

COMPARATIVE EXAMPLE B

To determine the activity of the Pt-Mg components in the absence of the zeolite component, a catalyst was prepared by adding 5 gm MgO (12/20 mesh Harshaw magnesia catalyst, MG-0601) to 10 ml of a solution containing deionized water and 0.7 gm of a 10% solution of $H_2PtCl_6 \cdot 6H_2O$. Water was permitted to evaporate slowly (e.g., overnight).

This catalyst was calculated to contain 0.5% Pt by weight on MgO. After drying at 75° C., the catalyst was calcined at 500° C. in a muffle furnace. 5.0 gm of the catalyst was loaded into a quartz microreactor, reduced under $H_2$ at 500° C., then screened for activity for propane conversion at 600° C. at a propane WHSV=0.9 hr.$^{-1}$.

For comparison, a quartz microreactor was packed with low surface area quartz chips. The reactor was heated to 600° C. and propane was passed through the reactor at the same flow rate used during catalyst screening. Product selectivities and propane conversion observed at 600° C. for the Pt-MgO catalyst and for the thermal reaction are given below.

| Catalyst | Pt-MgO | None (Quartz Chips) |
|---|---|---|
| Products, Wt. % | | |
| $H_2$ | 4.3 | 2.2 |
| $CH_4$ | 11.9 | 17.3 |
| $C_2H_6$ | 1.2 | 1.7 |
| $C_2H_4$ | 15.2 | 28.9 |
| $C_3H_6$ | 58.6 | 44.7 |
| $C_4H_{10}$ | 6.4 | 5.0 |
| $C_4H_8$ | 0 | 0 |
| Bz | 0.2 | 0 |
| Tol | 0 | 0 |
| $C_8A$ | 0 | 0 |
| $C_9A$ | 0 | 0 |
| $C_{10}+$ | 0 | 0 |
| Propane Conversion | 6.5 | 4.6 |

The foregoing Examples and Comparative Examples illustrate that neither the zeolite component nor the modifying metals alone give this high selectivity to propylene. However, the combination of the zeolite and the modifying metals give a catalyst which is more active for propane conversion and more selective for propylene than either component individually.

What is claimed is:

1. A process for converting propane to propylene, said process comprising contacting said propane under sufficient dehydrogenation conditions with a catalyst comprising ZSM-12, said catalyst further comprising:
   (i) a magnesium and/or manganese modifier; and
   (ii) a platinum modifier.

2. A process according to claim 1, wherein the amount of modifiers (i) and (ii) is at least twice the amount capable of being occupied by all of the cation exchange sites of said ZSM-12, and wherein the modifiers are either in the form of oxides of said magnesium, manganese and platinum or occupying cation exchange sites of said ZSM-12.

3. A process according to claim 1, wherein said catalyst further comprises a binder material.

4. A process according to claim 3, wherein said modifier (i) is magnesium.

5. A process according to claim 4, wherein said catalyst comprises from about 0.1 to about 10 percent by weight of magnesium and at least about 0.1 percent by weight of platinum, calculated on the basis of the elemental metals magnesium and platinum.

6. A process according to claim 3, wherein said modifier (i) is manganese.

7. A process according to claim 6, wherein said catalyst comprises from about 0.1 to about 10 percent by weight of manganese and at least about 0.1 percent by weight of platinum, calculated on the basis of the elemental metals manganese and platinum.

8. A process according to claim 1, wherein at least 20 percent of the propane contacted with said catalyst is converted and at least 75 percent by weight of the conversion products is propylene.

9. A process according to claim 1, wherein said dehydrogenation conditions comprise a temperature of from about 300° C. to about 700° C., a pressure of from about 0.1 atmosphere to about 10 atmospheres and a weight hourly space velocity of propane of from about 0.1 to about 20.

* * * * *